United States Patent [19]
Hanada et al.

[11] Patent Number: 5,945,103
[45] Date of Patent: Aug. 31, 1999

[54] PROCESS FOR PRODUCING THROMBIN

[75] Inventors: Shinichi Hanada; Yoshinobu Honda; Yasuaki Morisada; Shoichi Miyake; Isahiko Matsumoto, all of Osaka, Japan

[73] Assignee: The Green Cross Corporation, Osaka, Japan

[21] Appl. No.: 08/750,812

[22] PCT Filed: May 18, 1995

[86] PCT No.: PCT/JP95/00952

§ 371 Date: May 5, 1997

§ 102(e) Date: May 5, 1997

[87] PCT Pub. No.: WO95/31536

PCT Pub. Date: Nov. 23, 1995

[30] Foreign Application Priority Data

May 18, 1994 [JP] Japan .................................. 6-127094

[51] Int. Cl.⁶ .................................................. A61K 38/48
[52] U.S. Cl. ........................ 424/94.64; 435/214; 530/384
[58] Field of Search ........................ 424/94.64; 435/214; 530/384

[56] References Cited

U.S. PATENT DOCUMENTS

| | | | |
|---|---|---|---|
| 4,540,573 | 9/1985 | Neurath et al. | 424/85 |
| 4,764,369 | 8/1988 | Neurath et al. | 424/89 |
| 4,923,815 | 5/1990 | Tanaka et al. | 435/183 |
| 5,130,244 | 7/1992 | Nishimaki et al. | 435/188 |
| 5,138,034 | 8/1992 | Uemura et al. | 530/413 |
| 5,143,838 | 9/1992 | Kraus et al. | 435/214 |
| 5,151,355 | 9/1992 | Crowley et al. | 435/214 |
| 5,151,499 | 9/1992 | Kamayama et al. | 530/381 |
| 5,304,372 | 4/1994 | Michalski et al. | 424/94.64 |
| 5,354,682 | 10/1994 | Kingdom et al. | 435/214 |
| 5,506,127 | 4/1996 | Probe et al. | 435/214 |
| 5,525,498 | 6/1996 | Boctor et al. | 435/214 |
| 5,723,123 | 3/1998 | Karges et al. | 424/94.65 |

FOREIGN PATENT DOCUMENTS

| | | |
|---|---|---|
| 0543178 | 5/1993 | European Pat. Off. . |
| 4-211372 | 8/1992 | Japan ................ C12N 9/74 |

OTHER PUBLICATIONS

Seegers, Proc. Soc. Exp. Biol. Med., vol. 72(3), pp. 677–680, 1949.
Engel et al., J. Biol. Chem, vol. 216(5), pp. 1213–1221, 1971.

*Primary Examiner*—Chhaya D. Sayala
*Attorney, Agent, or Firm*—Sughrue, Mion, Zinn, Macpeak & Seas, PLLC

[57] ABSTRACT

The present invention provides a production method of thrombin which can convert prothrombin into thrombin highly efficiently even in the absence of thromboplastin and blood plasma, easily obtain a starting material for use in the conversion of prothrombin into thrombin, and prepare and purify thrombin in an industrial scale. It is characterized in treating a prothrombin-containing aqueous solution with a Ca salt at 0 to 15° C.

11 Claims, No Drawings

PROCESS FOR PRODUCING THROMBIN

TECHNICAL FIELD

This invention relates to a method for the production of thrombin.

BACKGROUND ART

Thrombin is a serine protease having a molecular weight of about 34,000 and an isoelectric point of about 7.1, namely a proteolytic enzyme which exerts its action at the final stage of the blood coagulation process. That is, it acts upon fibrinogen to form fibrin, thereby generating its blood coagulation function.

Because of this, thrombin is used clinically as a topical styptic in the surgical field and as a styptic of upper gastrointestinal bleeding and the like in the field of internal medicine.

In the living body, thrombin is present in the form of prothrombin as its precursor and formed by receiving limited hydrolysis with activated factor X and the like. In general, thrombin is produced by firstly extracting and purifying prothrombin from human blood plasma as the material and then treating the thus purified prothrombin with throinboplastin and the like. In other words, conversion into thrombin is carried out using purified prothrombin.

Thus, it is the present situation that thrombin is produced through several steps, starting from (1) purification of prothrombin as described above, followed by (2) conversion of prothrombin into thrombin and then (3) purification of thrombin and other necessary steps.

Based on this method, various modification methods have been reported. For example, there are known methods in which blood plasma treated with citric acid is allowed to contact with an anion exchanger, the thus adsorbed prothrombin is converted into thrombin on said exchanger and then the converted product is eluted and recovered (U.S. Pat. No. 5,143,838, European Patent Publication No. 378798) and in which blood plasma is treated with low temperature ethanol and then with an anion exchanger, and the thus purified prothrombin is converted into thrombin which is subsequently purified by a cation exchanger treatment [Unexamined Published Japanese Patent Application No. 3-128398 (U.S. Pat. No. 5,138,034, European Patent Publication No. 408029)].

Of these steps, conversion into thrombin is effected for example by a method in which a snake venom is used or a method in which a high concentration citric acid salt is used [Unexamined Published Japanese Patent Application No. 4-365481 and Unexamined Published Japanese Patent Application No. 5-194261 (European Patent Publication No. 543178)], in addition to the aforementioned method in which thromboplastin is used. Also, Unexamined Published Japanese Patent Application No. 5-186369 (European Patent Publication No. 528701) and U.S. Pat. No. 5,143,838 describe about conversion of purified prothrombin into thrombin making use of calcium chloride.

In this connection, thromboplastin prepared from human placenta is mainly used for the aforementioned purpose, but it cannot always be said that it can be obtained in sufficient quantity because of a difficulty in preparing the material. The same problem also occurs in the case of the snake venom.

On the other hand, the spontaneous conversion with high concentration citric acid salt and the calcium chloride-aided conversion are still limited to a laboratory scale level and not established yet as industrial mass production methods.

In view of the above, the inventors of the present invention have attempted to develop a method for the industrial scale production of thrombin and accomplished the present invention as the result.

Accordingly, the object of the present invention is to provide a method in which the starting material for carrying out conversion of prothrombin into thrombin can be obtained easily and thrombin can be produced and purified in industrial scale.

DISCLOSURE OF THE INVENTION

The object of the present invention can be achieved by a method for the production of thrombin which comprises treating a prothrombin-containing aqueous solution with a Ca salt at 0 to 15° C.

More illustratively, the thrombin production method of the present invention roughly comprises (1) preparation of prothrombin-containing aqueous solution, (2) conversion of prothrombin into thrombin and (3) purification of thrombin.

(1) Preparation of prothrombin-containing aqueous solution

The prothrombin-containing aqueous solution to be used in the present invention is not particularly limited, provided that it contains blood plasma originated prothrombin or prothrombin complex or is a fraction containing them. The prothrombin-containing aqueous solution of the present invention is prepared using a starting material such as a supernatant fluid obtained by removing cryoprecipitate from blood plasma (de-cryo plasma) or Cohn's I+II+III fraction, II+III fraction, or III fraction. Preparation of the prothrombin-containing aqueous solution of the present invention from these starting materials can be made by a known method. For example, it can be made by a method in which adsorption on an inorganic salt is employed or by an anion exchanger treatment or an affinity chromatography.

According to the present invention, it is desirable to use a prothrombin complex.

The prothrombin complex to be used herein is a mixture of a blood coagulation factor, prothrombin (blood coagulation factor II), with other blood coagulation related factors. Examples of the other components to be included together with prothrombin include blood coagulation factors VII, IX, X and the like. It is not necessary to use a highly purified product, and a crude product can be used.

When a crude product is used, it results in an advantage in that the purification step can be simplified and the cost therefore can be reduced, because it is not necessary to carry out complete purification of prothrombin prior to its conversion treatment into thrombin.

Origin of the prothrombin complex is not particularly limited. For example, a bovine or human origin complex, desirably human origin, may be used.

Known means can be used for the preparation of a prothrombin complex (-containing aqueous solution). For example, the methods disclosed in Unexamined Published Japanese Patent Application No. 62-10019 and Unexamined Published Japanese Patent Application No. 3-128398 (U.S. Pat. No. 5,138,034, European Patent Publication No. 408029) can be used. More illustrative examples include a method in which a prothrombin complex is prepared by treating blood plasma with an anion exchanger and a method in which a prothrombin complex is prepared using de-cryo plasma obtained by removing cryoprecipitate from blood plasma.

Examples of the anion exchanger include DEAE base exchangers (for instance, DEAE-agarose, DEAE-dextran, DEAE-cellulose and the like) and QAE base exchangers (for example, QAE-agarose, QAE-dextran and the like).

The prothrombin complex obtained by the above means can be subjected to its conversion treatment into thrombin directly as the complex form.

(2) Conversion of prothrombin into thrombin (2-1) The prothrombin-containing aqueous solution obtained in the above step (1) is treated with a Ca salt at 0 to 15° C. The term "to treat with a Ca salt" as used herein means to add a Ca salt to the prothrombin-containing aqueous solution and carry out its conversion into thrombin. Illustrative examples of such treatment include a method in which a Ca salt solution is added to the prothrombin-containing aqueous solution, mixed by stirring and then allowed to stand still, and a method in which a solid Ca salt is directly added to the prothrombin-containing aqueous solution, mixed by stirring and then allowed to stand still, of which the method in which a Ca salt solution is added to the prothrombin-containing aqueous solution is preferred. Examples of the Ca salt include calcium chloride, calcium hydroxide, calcium acetate and the like. Its treating concentration is approximately from 10 to 50 mM. The amount of prothrombin to be used in the treatment is approximately from 1 to 100 units/ml. The treating temperature is preferably from 0 to 10° C. The treating time is about 1 to 5 days. In addition, the solution may have a pH value of approximately from 6 to 9, preferably from pH 7 to 8.

(2-2) As occasion demands, a known thrombin conversion method may be used in combination. Preferably, the Ca salt treating solution of (2-1) is allowed to undergo autocatalytic reaction in a high concentration citric acid salt solution to effect spontaneous conversion into thrombin. The conversion may be carried out at a temperature of from 20 to 40° C. for a period of from 1 to 10 days. Examples of the citric acid salt include sodium citrate and the like. Its concentration may be approximately from 10 to 40% (w/v). The solution may have a pH value of from 6 to 9, preferably from 7 to 8.

(3) Purification and other treatments of thrombin

The thus obtained thrombin in the above step (2) is purified by a known method. Examples of the purification method include cation exchanger treatment, ammonium sulfate fractionation treatment, affinity chromatography treatment (for instance, treatment using immobilized arginyl methyl ester or immobilized heparin) and the like. In this connection, further purification may be carried out by dialysis, ultrafiltration, gel filtration and the like known means.

By the above treatment, various types of contaminated protein (for example, fibrinogen, fibrin, $\alpha_1$ globulin, $\alpha_2$ globulin, $\beta$ globulin, $\gamma$ globulin, protease and the like) are substantially removed. The thus purified thrombin may have an approximate specific activity of from 500 to 2,000 units/$A_{280}$, preferably from 1,000 to 2,000 units/$A_{280}$.

In this connection, activity of thrombin can be obtained by a conventional measuring method. In a preferred method, it is obtained by measuring coagulation time with a BBL fibrometer or the like apparatus using human blood plasma as the fibrinogen source. More illustratively, the activity is obtained by keeping 0.1 ml of a test sample diluted to various ratio with physiological saline for 2 minutes at 37° C. and then measuring the coagulation time by adding 0.2 ml of blood plasma kept at 37° C. in advance.

Said thrombin is made into pharmaceutical preparations in the usual way.

That is, addition of fillers, heating, sterilization, bacterial filtration, dispensation in small portions, freeze-drying and the like treatments may be carried out as occasion demands, as well as other optional treatments such as dry heating treatment (Unexamined Published Japanese Patent Application No. 62-81327), liquid heating [Unexamined Published Japanese Patent Application No. 63-243032 (U.S. Pat. No. 4,923,815)], trialkyl phosphate treatment (Unexamined Published Japanese Patent Application No. 60-51116, U.S. Pat. Nos. 4,540,573 and 4,764,369, European Patent Publication No. 131740) and combination of trialkyl phosphate treatment with dry heating treatment (Unexamined Published Japanese Patent Application No. 3-218322, U.S. Pat. No. 5,151,499, European Patent Publication No. 378208).

Illustratively, the following steps can be employed after the thrombin conversion treatment.

(i) Trialkyl phosphate treatment: The converted thrombin is allowed to contact with a dialkyl phosphate or trialkyl phosphate having an alkyl group of 1 to 10, preferably 2 to 10, carbon atoms, particularly preferably in the presence of a surface active agent, thereby effecting inactivation of viruses (to be referred to as SD treatment hereinafter), and the SD treatment can be carried out in accordance with a known method (Unexamined Published Japanese Patent Application No. 7-33799). Most preferably, the SD treatment is carried out in the presence of benzamidines (benzamidine, p-aminobenzamidine and the like), basic amino acids (arginine, lysine and the like) or $\epsilon$-aminocaproic acid (EACA). Benzamidines may be added in an approximate amount of from 0.0001 to 0.1 M, basic amino acids in an approximate amount of from 0.1 to 1 M, and EACA in an approximate amount of from 1 to 10% (w/v) (each as the final concentration).

The surface active agent to be used in the aforementioned SD treatment is preferably a nonionic surface active agent such as a polyol fatty acid ester, a sorbitan fatty acid ester (a Span compound), a polyoxyethylene-sorbitan fatty acid ester (a Tween compound), a polyoxyethylene-alkylphenol ether (a Triton compound), a polyoxyeLhylene fatty acid ester, a polyoxyethylene higher alkyl ether or the like. Their illustrative examples include Tween 80 (or polysorbate 80), Triton X-100, sulfobetaine and the like.

(ii) Cation exchanger treatment: For example, the method described in *Biochem.*, 10(13), p.2501, 1971, can be used. Examples of the cation exchanger to be used include sulfoethyl types (sulfoethyl-dextran, sulfoethyl-agarose and the like), sulfopropyl types (sulfopropyl-dextran, sulfopropyl-agarose and the like), carboxymethyl types (carboxymethyl-dextran, carboxymethyl-agarose and the like), Amberlite IRC-50 and the like.

The cation exchanger treatment is carried out under such conditions that thrombin is isolated as a purified substance from other contaminants. Illustratively, adhesion of thrombin to the cation exchanger and its washing are carried out preferably using 0.01 to 0.05 M citrate buffer (pH: about 6 to 8) containing 0.01 to 0.1 M sodium chloride, or 0.01 to 0.2 M phosphate buffer (pH: about 6 to 8) containing 0.01 to 0.1 M sodium chloride. Also, it is desirable to effect its elution by the use of 0.05 to 0.3 M citrate buffer having an approximate pH value of 6 to 8.

(iii) Dry heating treatment: The thrombin solution is subjected to this treatment as a dry composition by freeze-drying it by a known method. The dry heating treatment is carried out at generally 30 to 100° C., preferably 55 to 85° C., for generally 3 to 200 hours, preferably 10 to 100 hours. In order to protect thrombin from the heat, a known stabilizing agent may be used, such as a saccharide (monosaccharides, disaccharides), a sugar alcohol (e.g., mannitol), an amino acid (particularly a basic amino acid, e.g., arginine), an organic carboxylic acid or a salt thereof (e.g., sodium citrate), an inorganic salt (e.g., sodium chloride) or the like.

BEST MODE OF CARRYING OUT THE INVENTION

The following inventive and test examples are provided to further illustrate the present invention, though they are not intended as a definition of the limits of the present invention.

INVENTIVE EXAMPLE 1

Preparation of prothrombin and thrombin

A two liter portion of de-cryo plasma obtained by freeze-thawing human blood plasma was allowed to contact with a DEAE-dextran (trade name, DEAE-Sephadex A-50; manufactured by Pharmacia Co.) which had been equilibrated in advance with a buffer solution (pH 7) composed of 0.075 M sodium chloride and 0.01 M sodium citrate, and the thus adsorbed prothrombin complex was washed with a buffer solution (pH 7) composed of 0.15 M sodium chloride and 0.01 M sodium citrate and then eluted with a buffer solution (pH 7) composed of 1 M sodium chloride and 0.01 M sodium citrate. The resulting eluate was dialyzed, mixed with 1/10 quantity of 3% calcium chloride and then subjected to 3 days of treatment at 5° C. In this case, a buffer solution (pH 7) composed of 0.75% sodium chloride and 0.5% sodium citrate was used as the dialysis solvent.

After adjusting to pH 7, to this were added tri-N-butyl phosphate (TNBP), Tween 80 and epsilon-aminocaproic acid (EACA) to respective final concentrations of 0.3% (w/v), 1% (w/v) and 4% (w/v), subsequently carrying out 6 hours of incubation at 30° C. to effect inactivation of viruses.

Next, the above reaction solution was adjusted to pH 6.7 and allowed to contact with a sulfopropyl-dextran (trade name, SP-Sephadex C-50; manufactured by Pharmacia Co.) which has been equilibrated in advance with a buffer solution (pH 6.7) composed of 0.04 M sodium chloride and 0.02 M sodium citrate, thereby effecting adsorption of thrombin alone. The resulting column was washed with a buffer solution (pH 6.7) composed of 0.04 M sodium chloride and 0.02 M sodium citrate, 0.1 M phosphate buffer (pH 6.5) and 0.045 M sodium citrate solution (pH 7) in that order, and then the adsorbed thrombin was eluted and isolated with 0.1 M sodium citrate solution (pH 7). The resulting eluate was concentrated using Pericon (nominal molecular weight cut-off of 10,000; manufactured by Millipore Co.) and passed through a bacterial filter to prepare purified thrombin (at least 1,000 units/$A_{280}$ in specific activity). The thus obtained thrombin, after adjustment of its ionic strength and activity, was dispensed in small portions, dry heating and then subjected to 72 hours or more of freeze drying treatment at 60° C. or 80° C.

INVENTIVE EXAMPLE 2

The procedure of Inventive Example 1 was repeated, except that prothrombin was converted into thrombin by treating the eluate at 5° C. for 1 day in the presence of calcium chloride, in stead of the 3 days of treatment at 5° C. in the presence of calcium chloride, and subsequently adding trisodium citrate to a final concentration of 35% (w/v) and carrying out 2 days of treatment at pH 8 and at 37° C.

TEST EXAMPLE 1

Relationship between temperature condition and thrombin conversion efficiency at the time of the calcium chloride treatment was examined. The temperature condition of Inventive Example 1 was varied between 5 and 37° C. and tie thrombin conversion efficiency was measured under each condition. In this case, a thrombin conversion efficiency when the calcium chloride treatment was carried out at 15° C. for 3 hours by further adding 1/10 quantity of thromboplastin was defined as 100%. The results are shown in Table 1.

TABLE 1

| Temp. (°C.) | Treating time (day) | Conversion efficiency (%) |
|---|---|---|
| 5 | 3 | 89 |
| 15 | 3 | 71 |
| 25 | 3 | 30 |
| 30 | 2 | 14 |
| 37 | 2 | 2 |

TEST EXAMPLE 2

Examination was made on the effect of a single Ca salt treatment and a combination of the Ca salt treatment with a high concentration citric acid salt treatment on the thrombin conversion efficiency. The results are shown in table 2. In this connection, the criterion of conversion efficiency is as describe in Test Example 1.

TABLE 2

| Ca salt treatment | Citrate treatment | Conversion efficiency (%) |
|---|---|---|
| 5° C., 3 days | none | 89 |
| 5° C., 1 day | 37° C., 2 days | 89 |

COMPARATIVE EXAMPLE 1

Prothrombin was extracted as a simple substance from Cohn's II+III fraction with 0.1 M sodium chloride solution. The thus obtained extract was adjusted to pH 6.7, mixed with 1% calcium chloride (1/10 quantity), thromboplastin (1/10 quantity) and blood plasma (1/40 quantity) and then incubated at 20° C. for 3 hours. The reaction solution was allowed to contact with an anion exchanger (SP-Sephadex C-50, manufactured by Pharmacia Co.) which has been equilibrated in advance with 0.1 M phosphate buffer (pH 6.5), and the adsorbed thrombin was eluted with 0.1 M citrate buffer (pH 6.7). The resulting eluate was mixed with 0.3% (w/v) TNBP, 1% (w/v) Tween 80 and 4% (w/v) EACA and incubated at 30° C. for 6 hours (SI) treatment). The thus obtained reaction solution was applied to a column packed with an immobilized heparin (Heparin Toyopearl, manufactured by Tosoh Corporation) which has been equilibrated in advance with 0.02 M citrate buffer (pH 7.0), and thrombin was eluted with 0.3 M citrate buffer (pH 6.0). The resulting eluate was concentrated using an ultrafiltration membrane (nominal molecular weight cutoff of 10,000) and passed through a bacterial filter to prepare purified thrombin.

TEST EXAMPLE 3

Properties of the thrombin of the present invention obtained in Inventive Example 1 were compared with those of the purified thrombin prepared from Cohn's II+III fraction in Comparative Example 1 and of a commercial thrombin preparation (manufactured by The Chemo-Sero-Therapeutic Research Institute).

(1) Specific activity

Thrombin activity and absorbance at 280 nm of each sample were measured to calculate and compare its specific activity. As the results, specific activity of the thrombin of the present invention was 1,000 units/$A_{280}$, while those of the II+III fraction-originated thrombin and the commercial product were 555 units/$A_{280}$ and 582 units/$A_{280}$, respectively.

(2) Distribution

Results of cellulose acetate electrophoresis showed that β fraction of the thrombin of the present invention was 100%, while those of the II+III fraction-originated thrombin and the commercial product were 55% and 92%, respectively.

(3) Molecular weight measurement

When measured by SDS-PAGE electrophoresis (Fast System, manufactured by Pharmacia Co.), the thrombin of the present invention was found as a single band of 34,000 in molecular weight under non-reducing condition, while bands of other than 34,000 in molecular weight were found on higher and lower molecular weight sides in the II+III fraction-originated thrombin and the commercial product.

INDUSTRIAL APPLICABILITY

Prothrombin can be converted into thrombin highly efficiently by the production method of the present invention even in the absence of thromboplastin and blood plasma. Also, according to the production method of the present invention, starting material for use in the conversion of prothrombin into thrombin can be obtained easily and prepared efficiently by a simple procedure, so that cost and labor can be reduced sufficiently.

Also, employment of the known high concentration citrate treatment (Unexamined Published Japanese Patent Application No. 4-365481) after the Ca salt treatment renders possible shortening of the treating period (including Ca salt treatment or citrate treatment) without reducing conversion efficiency of prothrombin into thrombin. The treatment with high concentration citrate may be carried out using 10 to 40% (w/v) of a citric acid salt at 20 to 40° C. for 1 to 10 days. Also, the use of a prothrombin complex as the source of prothrombin can save labor for complete purification into prothrombin. In addition, the conversion efficiency into thrombin can further be improved by carrying out the Ca salt treatment at 0 to 10° C. In consequence, the method of the present invention is a useful method suitable for industrial scale production.

We claim:

1. A method for producing thrombin which comprises treating a prothrombin-containing aqueous solution with a Ca salt at 0 to 15° C. to produce a calcium salt-treated solution containing thrombin.

2. The method for producing thrombin according to claim 1 wherein said Ca salt-treated solution is further treated with 10 to 40% (w/v) of a citric acid salt at 20 to 40° C. for 1 to 10 days.

3. The method for producing thrombin according to claim 1 wherein prothrombin is in the form of a prothrombin complex.

4. The method for producing thrombin according to claim 1 wherein the Ca salt treatment is carried out at 0 to 10° C.

5. The method for producing thrombin according to claim 1 wherein the Ca salt treatment is carried out for 1 to 5 days.

6. The method for producing thrombin according to claim 1 wherein the Ca salt treatment is a step in which prothrombin is converted into thrombin in the presence of a Ca salt.

7. The method for producing thrombin according to claim 1 wherein the Ca salt is calcium chloride, calcium hydroxide or calcium acetate.

8. The method for producing thrombin according to claim 1 wherein the Ca salt treatment is carried out in the absence of thromboplastin and blood plasma.

9. The method for producing thrombin according to claim 1 wherein the Ca salt treatment is carried out on a prothrombin complex-containing aqueous solution.

10. The method for producing thrombin according to claim 1 wherein (1) a trialkyl phosphate treatment, (2) a cation exchanger treatment and (3) a dry heating treatment are carried out after the Ca salt treatment.

11. The method according to claim 1, wherein the calcium salt-treated solution that is produced is a thrombin-containing preparation having a specific activity of at least 1,000 units/$A_{280}$.

* * * * *